US006533255B1

(12) United States Patent
Mitsuhashi et al.

(10) Patent No.: US 6,533,255 B1
(45) Date of Patent: Mar. 18, 2003

(54) LIQUID METAL-HEATING APPARATUS FOR BIOLOGICAL/CHEMICAL SAMPLE

(75) Inventors: Masato Mitsuhashi, Irvine, CA (US); Charles Y. Chu, Rolling Hills Estates, CA (US)

(73) Assignees: Hitachi Chemical Research Center, Inc., Irvine, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/980,985

(22) PCT Filed: May 12, 2000

(86) PCT No.: PCT/US00/13220

§ 371 (c)(1), (2), (4) Date: Oct. 23, 2001

(87) PCT Pub. No.: WO00/69561

PCT Pub. Date: Nov. 23, 2000

Related U.S. Application Data

(60) Provisional application No. 60/134,264, filed on May 14, 1999, and provisional application No. 60/145,875, filed on Jul. 27, 1999.

(51) Int. Cl.[7] .......................... F02M 15/00; C10K 1/08; C12Q 1/68; C12P 19/34

(52) U.S. Cl. ........................ 261/149; 261/151; 261/152; 261/153; 261/155; 261/435; 261/6; 261/91.1; 261/91.2

(58) Field of Search ................................ 261/149, 150, 261/152, 153, 155; 435/6, 91.1, 91.2

(56) References Cited

U.S. PATENT DOCUMENTS

| | | | | |
|---|---|---|---|---|
| 3,716,045 | A | 2/1973 | Vollhardt | 126/360 A |
| 4,037,653 | A | 7/1977 | Meissmer | 165/1 |
| 4,750,551 | A | 6/1988 | Casey | 376/367 |
| 5,508,197 | A | 4/1996 | Hansen et al. | 435/285.1 |

*Primary Examiner*—Jezia Riley
(74) *Attorney, Agent, or Firm*—Knobbe, Martens, Olson & Bear LLP

(57) ABSTRACT

An apparatus for temperature control of biological/chemical samples employing liquid metal is described. A gallium-indium alloy may be used to provide excellent temperature control. Methods of using liquid metal to provide temperature control for biological/chemical samples are also described. A preferred use for the described liquid metal-heating apparatus is to provide precise temperature control for polymerase chain reaction (PCR).

42 Claims, 8 Drawing Sheets

LIQUID METAL-HEATING APPARATUS FOR BIOLOGICAL/CHEMICAL SAMPLE

This application claims the benefit of Provisional application Ser. No. 60/134,264, filed May 14, 1999, and Provisional application Ser. No. 60/145,875, filed Jul. 27, 1999.

BACKGROUND OF THE INVENTION

1. Field of the Invention

The present invention relates to a heating apparatus for biological/chemical samples, which device includes PCR thermal cyclers. The present invention relates also to a method of heating biological/chemical samples, which method includes PCR.

2. Description of the Related Art

The polymerase chain reaction (PCR) has become a widely used tool in molecular biology. This technique allows one to quickly and easily amplify segments of nucleic acid for further investigation and analysis. Roughly two types of automated PCR instruments are conventionally available on the market.

The first type is based on a robotic arm (such as RoboCycler™ from Stratagene). In this type, temperature control is accomplished by using a stationary heating block, and samples are transferred mechanically between blocks set at different temperatures according to programmed steps. The samples are moved by the robotic arm in either a circular or linear direction. The heating blocks comprise wells in which test tubes (or micro titer plate) are fitted, and it is normally necessary to fill the wells with either water or mineral oil for sufficient heat transfer.

The second type is a fully integrated and dedicated PCR thermocycler. The PCR thermocycler relies on a thermoelectric element for the Peltier effect to provide rapid change of temperature. Depending on the direction of electric current, the thermoelectric element can either heat or cool a sample on demand. Thermo-cycling parameters are programmed into a temperature controller.

The first type uses at least three heating blocks whose temperatures are set at 55° C., 72° C., and 94° C., respectively. The second type uses a thermocycler with a heating block whose temperature is controlled to change to 55° C., 72° C., and 94° C. in one cycle. Conventional heating blocks have a plurality of wells for receiving test tubes, and the heating blocks heat the test tubes with an electric resistance, for example, and cool them by circulating a liquid through elaborate channels inside the heating blocks or by a thermoelectric element, for example. The fluid for cooling is commonly a water-based medium. The elaborate channels for cooling are machined into the holding blocks to allow either tap water or refrigerated water to circulate throughout. Although such a setup can give very high cooling rates, high costs are associated with this system and make this type of configuration unacceptable. Thus, a combination of an electric resistance and a thermoelectric element provided in a metal heating block is the most frequently used configuration.

The holding block is specifically machined to fit a particular brand of test tubes in order to provide a maximized contacting surface to enhance heat transfer. The holding blocks are made interchangeable to accommodate an assortment of different test tubes or microtiter plates from different vendors. Even if the surface of the holding block is precisely machined, the area actually contacting each sample holder (i.e., test tube or microtiter plate) may vary due to minor imperfections in plastic injection molding. A variety of methods are employed to alleviate this problem, including force clamping and adding mineral oil, to fill the gap between the surface of a holding block and the surface of a sample holder. As the number of samples subjected to the holding block increases, means to ensure temperature uniformity between different samples become important.

Further, the heating block itself has temperature distribution. If the heating block has 96 wells, wells at different corners may have different temperatures.

Although heat transfer difference may occur at contacting surfaces between test tubes and respective wells, and uneven heat diffusion may occur within the heating block, there is no way to verify the accuracy of the temperature. Users must rely on a temperature indicator installed in the heating block.

In addition, the wells of the heating block are designed specifically for particular test tubes, and thus, a 96-well format heating block cannot be used for any other format PCR plates such as a 384-well format. Further, one heating block holds only one PCR plate.

SUMMARY OF THE INVENTION

To guarantee the success of experiments and allow users to directly compare samples from the same run or different runs at different times using the same program, it is essential to have all samples reach the same temperature during each cycle. The uniformity of heating and cooling rates across the entire holding block surface, as well as the physical fit between wells and test tubes, are very important.

In accordance with the present invention, an improved polymerase chain reaction thermal cycler can be implemented based on liquid metals. The invention is based on the realization that liquid metals have a comparable heat conductivity and capacity to that of metal and at the same time are not confined to having a pre-defined shape. This enables the use of sample test tubes from different vendors without switching test tube holding blocks. Precise temperature control and rapid temperature cycling is carried out by liquid metals. In addition, pumping and switching of liquid metal can be based on magnetohydrodynamics. Furthermore, in one embodiment, multiple plates can be treated at one time when using a large liquid metal bath. By using a large liquid metal bath comprising a plurality of heating and cooling sections, which bath has a length sufficient to complete PCR cycles without physically circulating test tubes in the bath, continuous input of samples and continuous output of PCR products can be performed simultaneously, resulting in surprisingly high productivity.

The present invention can be adapted to any type of heating and cooling device for biological/chemical samples which require accurate temperature control. The claimed invention is directed to an apparatus for temperature control of samples comprising at least one container containing liquid metal, said container having an upper open area where the liquid metal thermally contacts one or more of the samples for temperature control thereof; and a temperature control device for heating the liquid metal, whereby said liquid metal remains in a liquid state and does not significantly evaporate during heating.

The container containing the liquid metal may be either a plastic or metal container. The temperature control device for heating the liquid metal may be the heat block of a thermal cycler.

A variety of liquid metal compositions may be used in the practice of the claimed invention. Compositions containing gallium may be preferred. A most preferred composition may be a 75.5% gallium/24.5% indium alloy.

The apparatus of the presently claimed invention may include a plurality of containers containing liquid metal and one sample container. The sample container may then be moved through a series of containers containing liquid metal by any convenient means such as manually or mechanically, for example, by use of a robotic arm.

Alternatively, the liquid metal may be moved through the sample container. The liquid metal at a first temperature may be replaced by liquid metal of a second temperature. Movement of the liquid metal, either within the sample container or its injection and removal from the sample container may be accomplished by a conventional pump. Alternatively, movement of the liquid metal may be accomplished by magnetohydrodynamics in either AC or DC mode. Of course, gravity may also be used to move the liquid metal.

The containers containing liquid metal may also be linked to other apparatus for sample treatment such as a robotic liquid handler and dispenser, a cell incubator and/or a detection system such as a Luminex 100, for example.

The claimed apparatus may be used in a method of incubating one or more biological/chemical samples at a pre-determined temperature comprising contacting the one or more biological/chemical samples with a container containing liquid metal at the pre-determined temperature for a given time period. This method may further comprise movement of biological/chemical samples between a plurality of containers. This movement may be accomplished mechanically by use of a robotic arm, for example, or manually. In one embodiment, the temperature of the plurality of containers containing liquid metal are 30–65° C., 65–85° C. and 85–100° C., respectively.

The claimed invention also encompasses a method of varying the temperature of a sample in a single container comprising:

(a) incubating a biological/chemical sample in contact with a container containing liquid metal at a pre-determined temperature for a given time period;

(b) changing the temperature of the liquid metal to a pre-determined temperature which is different from the predetermined temperature of step (a); and (c) repeating steps (a) and (b) until all desired incubations have occurred.

Various means for varying the temperature of the single sample container may be used. The temperature change may be affected by replacing liquid metal at a pre-determined temperature with liquid metal at a different pre-determined temperature. The liquid metal may be moved throughout the container by magnetohydrodynamics. Magnetohydrodynamics may be operated in either AC or DC mode. Alternatively, the liquid metal may be moved throughout the container by means of a pump or gravity may be used to move the liquid metal.

The liquid metal composition of the claimed method may be gallium or a composition containing gallium. A preferred composition may comprise 75.5% gallium and 24.5% indium.

A preferred method using the apparatus of the present disclosure may be a method of performing polymerase chain reaction (PCR). Typically, a PCR cycle comprises:

denaturing a polynucleotide sample in thermal contact with liquid metal at a temperature of about 90–98° C. for about 10–90 seconds;

hybridizing oligonucleotide primers to the denatured polynucleotide template in thermal contact with liquid metal at a temperature of about 30–65° C. for about 1–2 minutes; and synthesizing a new polynucleotide strand incorporating the oligonucleotide primer and using the denatured polynucleotide as template for a polymerase in thermal contact with liquid metal at a temperature of about 70–75° C. for about 30 seconds to 5 minutes.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow, although the present invention is not limited thereto.

BRIEF DESCRIPTION OF THE DRAWINGS

These and other features of this invention will now be described with reference to the drawings of preferred embodiments which are intended to illustrate and not to limit the invention.

FIG. 2(*a*) is a schematic side view, and FIG. 2(*b*) is a schematic plane view (showing the directions of a magnetic field and a electrical field).

FIG. 3(*a*) is a schematic plane view, and FIG. 3(*b*) is a schematic side view (showing the directions of a magnetic field and a electrical field).

DETAILED DESCRIPTION OF THE PREFERRED EMBODIMENT

Liquid Metal

Figure 1:
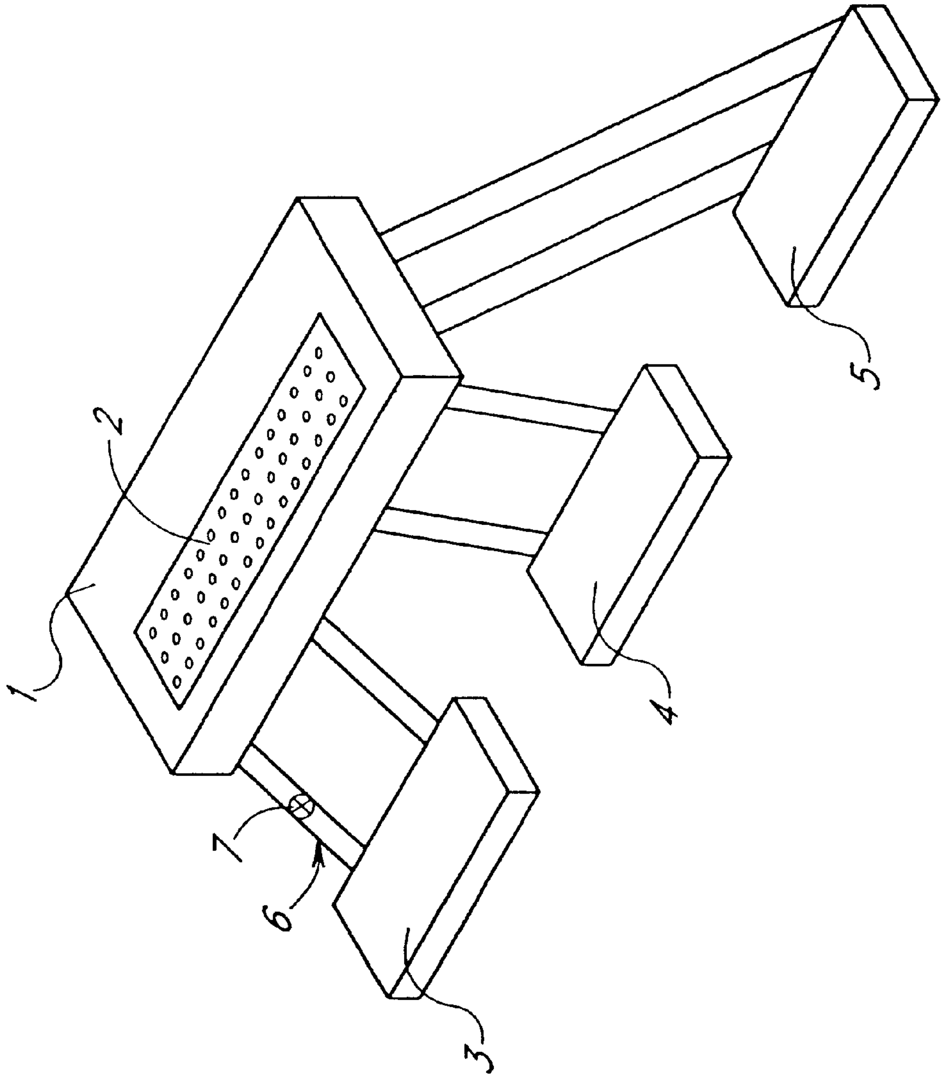
FIG. 1 is a schematic side view showing an embodiment of the apparatus of the present invention, in which a single set of samples is connected to three separate containers containing liquid metal.

By using liquid metal as a heating and cooling medium for a heating block, full contact with test tubes can be achieved, resulting in uniform heat transfer regardless of the type, size, and shape of test tubes. Pre-formed wells are no longer required. Furthermore, uniformity of temperature within the heating block can be achieved, because liquid metal can easily be circulated in the heating block by convection or by external force.

In this regard, one advantage of using liquid metal is that formation of flow is easily achieved. When liquid metal is exposed to a magnetic field formed in one direction and an electrical field formed in a direction perpendicular to the direction of the magnetic field, the liquid metal flows in a direction perpendicular to both the direction of the magnetic field and the direction of the electrical field. By using a magnetic field and an electrical field, it is possible to cause liquid metal to flow in a designated direction without physical control such as control by a pump. These characteristics can be used to make the temperature within the heating block uniform by convection or to introduce and discharge liquid metal into and from the heating block. In an alternate embodiment a pump may be used. If the electrical field is formed by DC power, and its frequencies change, flow of the liquid metal rapidly oscillates in accordance with the frequencies, thereby achieving high uniformity of temperature.

Liquid metal is flowable during operation and has an evaporation point higher than operation temperature. Further, liquid metal is preferably non-toxic under conditions of operation. Liquid metal has high heat and electrical conductivity and thus can be very responsive to heating and cooling patterns/cycles. For PCR, rapid heating and cooling rates are required (such as 4–20° C. per second), which liquid metal can satisfy.

Liquid metal is available on the market for very specific and exclusive uses, i.e., as a coolant for nuclear power plants where top level control management is required for safety. Liquid metal is not something biologists normally consider. However, the present inventors discovered that some liquid metals could be very useful as heating blocks without the issue of toxicity and other problems. A well-known liquid metal is mercury. However, mercury is not usable in the present invention, because it partially vaporizes at room temperature and is highly toxic.

A variety of liquid metal compositions may be used in the practice of the claimed invention. Compositions containing 60–100% gallium in combination with indium may be preferred. Some compositions also contain tin and zinc. Some specific examples include: 61% gallium/25.0% indium/13.0% Sn/ 1.0% Zn; 62.5% gallium/21.5% indium/ 16.0% Sn; 75.5% gallium/24.5% indium; 95% gallium/5% indium; and 100% gallium. In a preferred embodiment the liquid metal may be a gallium-indium alloy comprising 75.5% gallium and 24.5% indium. This alloy becomes a liquid at a temperature of 15.7° C. and it has a boiling point of 2,000° C. Thus, the gallium-indium alloy is in a liquid state but never evaporates during PCR. No toxic problem occurs. This alloy is safe even if it is ingested. Furthermore, this liquid metal can be washed off easily with dilute potassium hydroxide (KOH) even if the liquid metal adheres to test tubes and other containers. An effective concentration range is 0.001M–1M KOH. It does not easily adhere to skin.

In addition to heating blocks for polymerase chain reaction (PCR), the liquid metal heating blocks of the present invention can be used widely in the field of biotechnology and chemistry. Examples include but are not limited to incubations of enzymatic reactions such as restriction enzymes, biochemical assays and polymerase reactions; cell culturing and transformation; hybridization; and any treatment requiring precise temperature control. Based on the present disclosure, one of ordinary skill in the art can readily adapt the liquid metal technology to various analyses of biological/chemical samples which require accurate temperature control.

In a preferred embodiment, the liquid metal heating blocks of the presently claimed invention may be used for PCR. In a typical PCR cycle, the polynucleotide sample is denatured by treatment in a liquid metal bath at about 90–98° C. for 10–90 seconds. The denatured polynucleotide is then hybridized to an oligonucleotide primer by treatment in a liquid metal bath at a temperature of about 30–65° C. for 1–2 minutes. Chain extension then occurs by the action of a polymerase on the polynucleotide annealed to the oligonucleotide primer. This reaction occurs at a temperature of about 70–75° C. for 30 seconds to 5 minutes in the liquid metal bath. Any desired number of PCR cycles may be carried out.

In a most preferred embodiment, the denaturation of the polynucleotide may occur at a temperature of 94° C. for about 1 minute. The hybridization of the oligonucleotide to the denatured polynucleotide occurs at a temperature of about 37–65° C. for about one minute. The polymerase reaction is carried out for about one minute at about 72° C. All reactions are carried out in the same multiwell plate in a liquid metal bath of the claimed invention. About 30 PCR cycles may be preferred. The above temperature ranges and the other numbers are not intended to limit the scope of the invention. These ranges are dependant on other factors such as the type of enzyme, the type of container or plate, the type of biological sample, the size of samples, etc. One of ordinary skill in the art can readily modify the ranges as necessary.

Several embodiments included in but not limiting the present invention will be explained below.

Liquid Metal Magnetohydrodynamic PCR Thermal Cycler

In one embodiment of the present invention (FIG. 1), a thermal cycler includes a sample 2 and a sample container 1 and more than one container holding the liquid metal 3, 4, 5. In an embodiment, it is preferred to have the containers made out of plastic materials to prevent chemical reaction with liquid metal. The liquid metal inside each container is heated by a heating element to a specific temperature according to the need to complete PCR. Heating the sample to a specific temperature can be conducted by simply circulating the liquid metal in a loop passing a heating area where the test tubes or micro titer plate is placed 6. The test tubes or microtiter plates thermally contact the liquid metal. This may be accomplished by contacting the test tubes or microtiter plates with a container such as a plastic bag containing the liquid metal, for example. More preferably, in another embodiment, the test tubes or microtiter plates are in direct contact with the liquid metal. Changing the temperature of the heating area can be conducted easily by channeling each loop through the heating area by use of a valve 7. The liquid metal can flow by using magnetohydrodynamic force created by a magnetic field and an electrical field whose directions are perpendicular to each other.

Figure 2:
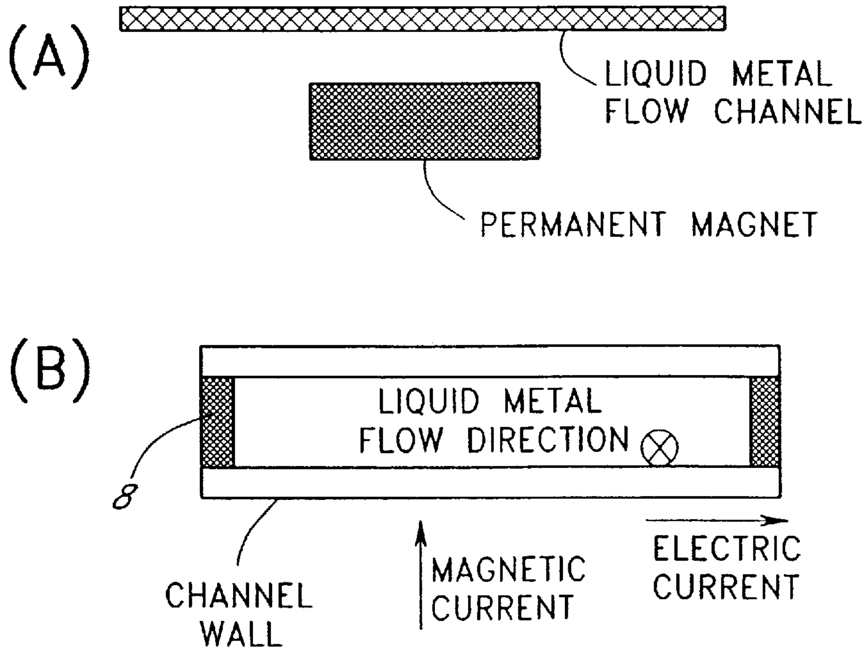
FIG. 2 illustrates magnetohydrodynamics using DC mode.
Figure 3:
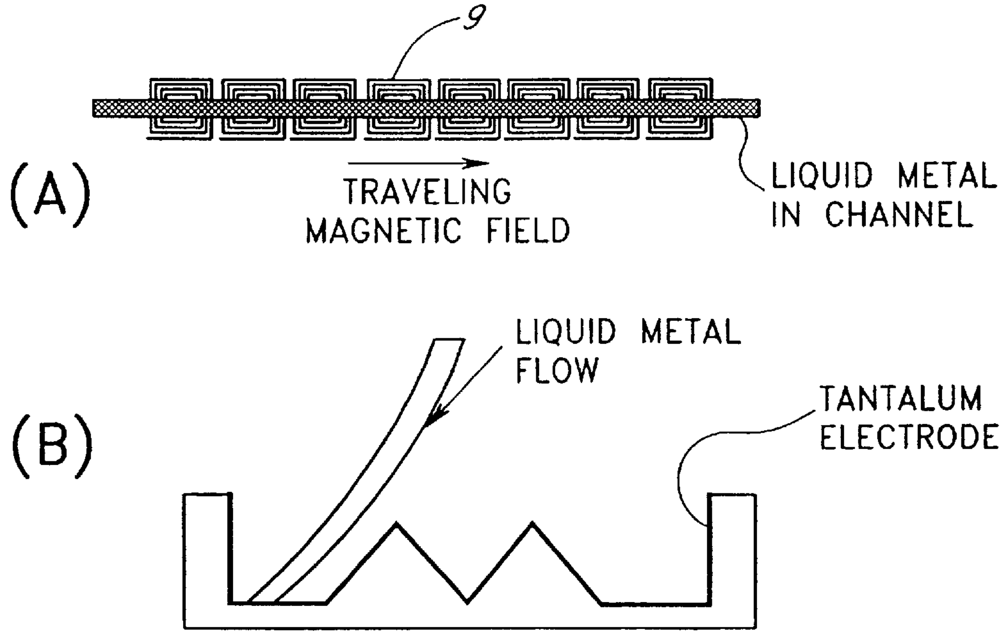
FIG. 3 illustrates magnetohydrodynamics using AC mode.

Pumping and switching of liquid metal flow is accomplished by magnetohydrodynamic. Two different modes of magnetohydrodynamic (MHD) flows, DC (direct current) and AC (alternating current), can be used. DC mode MHD is by far the simplest to implement (FIG. 2). It includes a pair of electrodes 8 contacting the liquid metal completing an electrical circuit and a magnetic field. The direction of electrical current flow, the magnetic field, and the flow of liquid metal should be mutually orthogonal to each other. When the electrical current is passed through the liquid metal, a magnetic field is created. This magnetic field would have a different orientation with respect to the external magnetic field. Therefore, the liquid metal will be pushed along the channel. No mechanical moving parts are required. DC mode MHD pumping is inherent. However, it requires the electrodes to come in contact with liquid metal. Another variation of MHD is AC mode (FIG. 3). It includes an inductor array 9 and an electronic controller. The electronic controller sets off a traveling magnetic wave in the inductor array. The traveling magnetic field wave introduces a current inside the liquid metal. The same current will push the liquid metal inside the channel in the same direction as the traveling magnetic field. In AC MHD, there is no need to have electrodes directly contacting the liquid metal itself. However, it is generally a bit more difficult to predict the performance of the pump. A switch mechanism is needed to divert the flow of liquid metal back to its corresponding temperature reservoir. This can be accomplished by using either DC or AC mode MHD. It simply deflects the flow of liquid metal from its gravity flow path.

Figure 4:
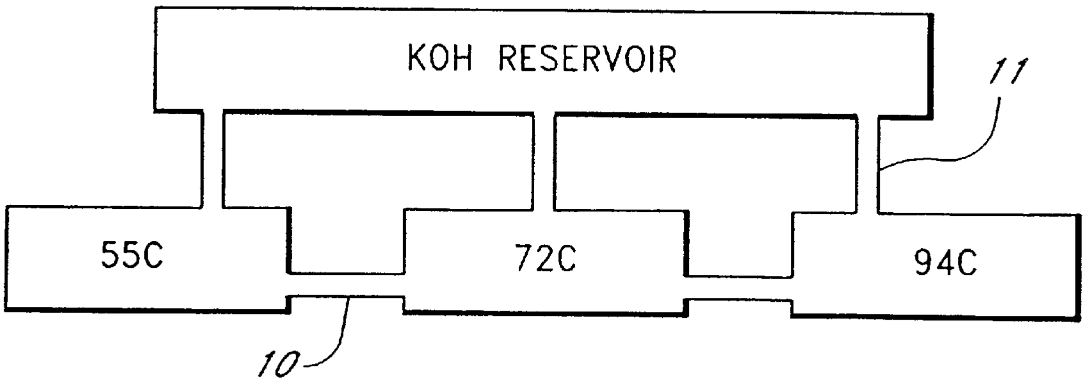
FIG. 4 shows connection of multiple reservoirs containing liquid metal with a KOH reservoir to prevent liquid metal oxidation.

Over time, the flow switch may accumulate into one particular reservoir more than another. Although this is not a problem in terms of temperature control, the volume of liquid metal under different temperatures would be different. To overcome this problem, a small tubing 10 is used to connect different reservoirs together (FIG. 4). The small tubing allows the liquid metal level to equilibrate, yet it does not significantly affect the temperature of each individual liquid metal reservoir.

To prevent liquid metal from degrading due to oxidation in the atmosphere, a light KOH solution is needed. Again, a small tubing 11 connects a KOH reservoir with different liquid metal reservoirs. The KOH solution should be cooled by means of a thermoelectric element to 4C after the thermal cycle is finished to preserve the sample. KOH solution can be pumped by either MHD or a conventional fluid handling pump. KOH solution is also conductive.

Figure 5:
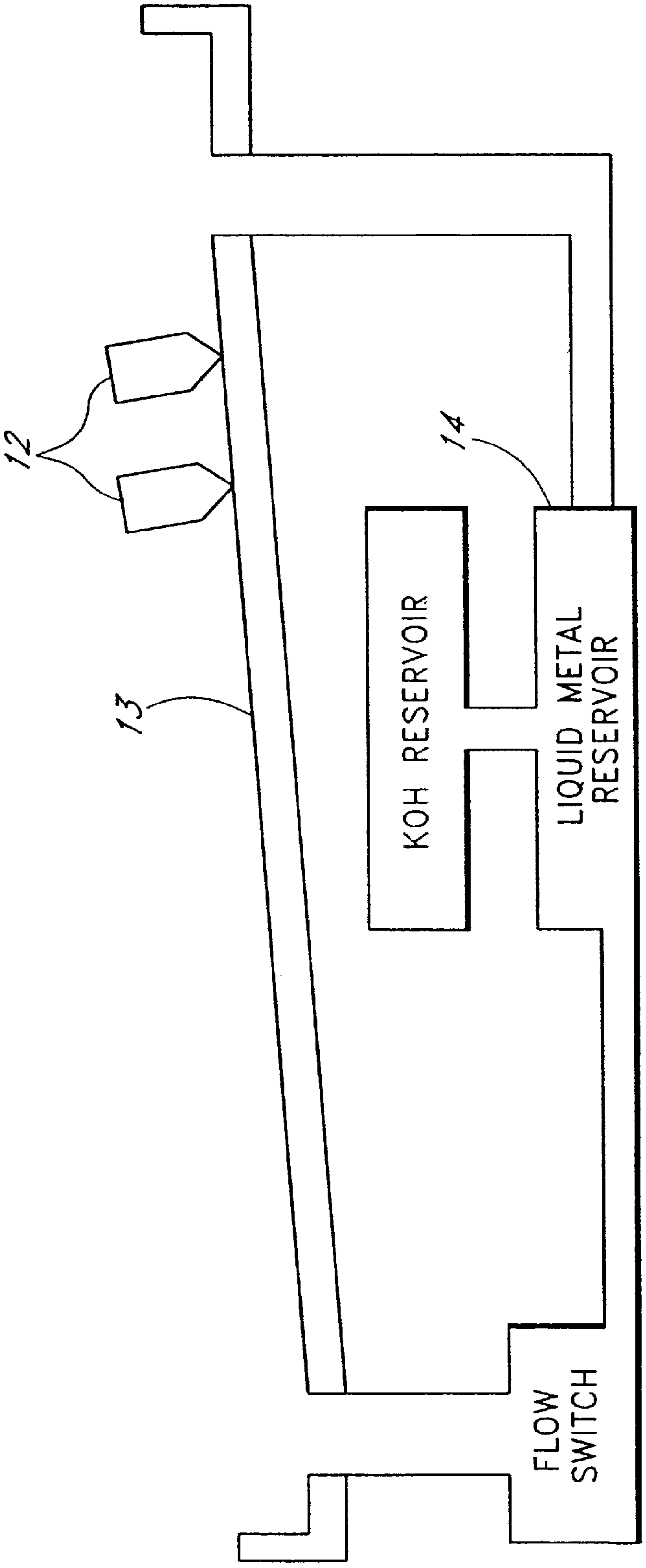
FIG. 5 is a schematic view showing an embodiment with a sloped ramp to facilitate movement of liquid metal around biological/chemical samples.

In an alternate embodiment, the test tubes 12 or micro titer plate are placed on a slightly sloped ramp 13 with openings in the upper and lower ends (FIG. 5). Once the liquid metal is pumped out of the upper opening, it will flow naturally by gravity towards the lower opening. The upper opening should allow flow of liquid metal covering the entire upper ramp surface. In normal embodiments, the depth of the liquid metal flow is such that it covers the depth of the sample inside the test tube or micro titer plate. In an embodiment, it is preferred to have a lower opening to collect the liquid metal to a small opening to be drained back to its corresponding reservoir 14 to be re-heated.

Universal Heating Block with Liquid Metal

One problem with thermal cyclers currently available is the unique physical design of the heat blocks of many of the thermal cyclers currently available. Because the use of a thermal cycler requires the use of consumable plastic microplates and/or trips of wells in which the reactions are performed, many manufacturers have chosen to uniquely configure their heat blocks thereby forcing a user to purchase their own brand of plastic consumables. That is, "generic" plastics commercially available from other sources won't fit onto the heat block. This restricts the freedom a researcher has in that he/she is forced to purchase plastics from only the manufacturer of his/her thermal cycler. A solution to this limitation would provide flexibility to the researcher in allowing a greater choice of plastics.

Figure 6:
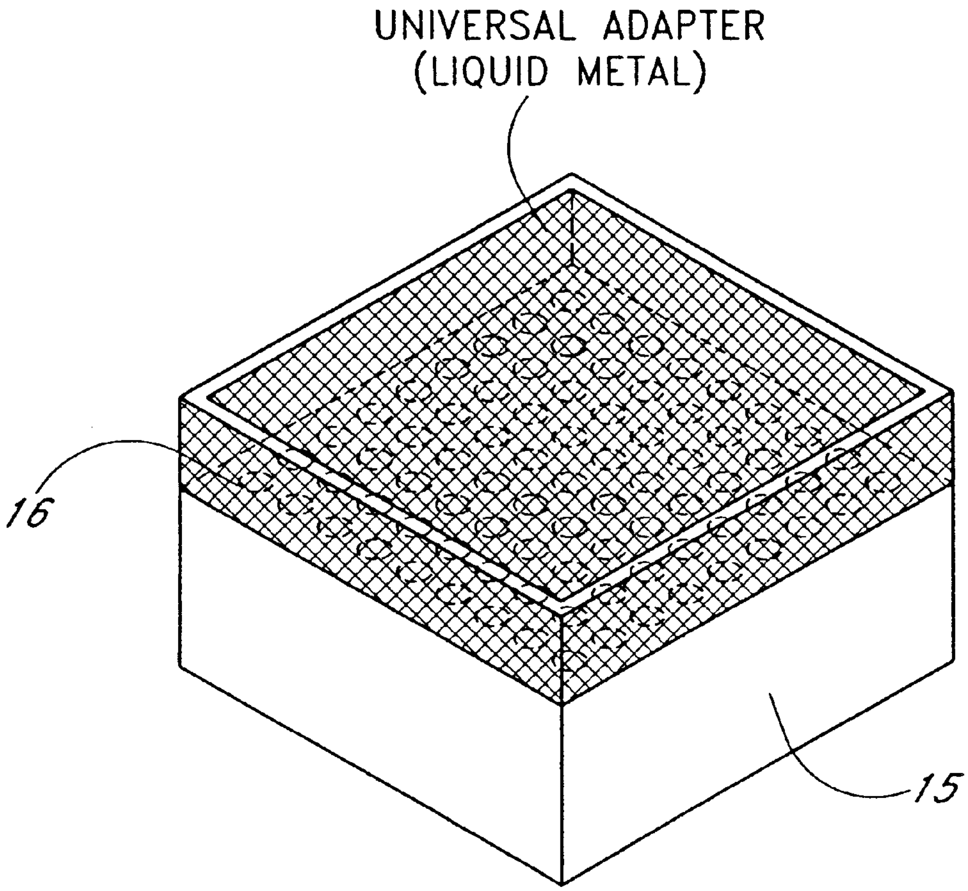
FIG. 6 is a schematic side view showing a liquid metal universal adapter for any microplate or well strip.

A second embodiment of the claimed invention presents a solution to the problem stated above, while maintaining a high level of temperature control. A universal adapter for any plastic microplate (including 96-well, 384-well and 1536-well) and strips of wells (including 8-well, 12-well or any portions or combinations thereof) functions on any commercially available thermal cycler (or equivalent). A liquid metal alloy bath is constructed from a container made of metal (brass, copper or other similar metals or combinations thereof) or plastic. A volume of the liquid metal alloy is then placed into the metal or plastic container (FIG. 6). This bath is placed in contact with the heat block of a conventional thermal cycler 15. The plastic part used for the reaction is placed into the liquid metal alloy bath 16. Caps and/or suitable cover are placed onto the plastic part to prevent evaporation during the run. The thermal cycler is then programmed and run as normal with the cover open. Given the excellent thermal conductivity properties of the liquid metal alloy bath, efficient, reliable, and reproducible temperature control is maintained throughout the run. In a preferred embodiment, a gallium-indium alloy may be used as the liquid metal. The gallium-indium alloy is a solid at 4° C. Since most thermal cycler runs are programmed to end at 4° C., the alloy freezes and allows very easy removal of the plastic part from the bath without any appreciable alloy adhering to the surface of the plastic.

Other advantages of the liquid metal alloy bath are that the lag time when changing temperature of a water bath is virtually eliminated. The liquid metal alloy bath provides excellent heat conductivity with minimal ramp times between different temperatures. Furthermore, there is no evaporation of the alloy, thus eliminating most user intervention and maintenance.

The liquid metal alloy bath may be designed to use on any commercially available heat block, including thermal cycler heat blocks, using any commercially available plastic consumables such as those designed for PCR.

In an alternate embodiment, the liquid metal alloy baths may be vertically stacked with heating elements sandwiched between the baths. This multi-bath configuration allows multiple consumables to be used for PCR simultaneously rather than sequentially. This approach provides an effective solution to satisfy the demands of high throughput and/or high volume applications.

Liquid Metal Robocycler

In this embodiment, there are a plurality of heating containers containing liquid metal and a heating device for each heating container containing the liquid metal. The samples are moved either manually or mechanically between the temperature blocks. In a preferred embodiment, the samples may be moved mechanically between different temperature blocks according to pre-programmed steps. The samples are moved by a robotic arm in either circular or linear movement.

Liquid Metal High Capacity Thermocycler

Figure 7:
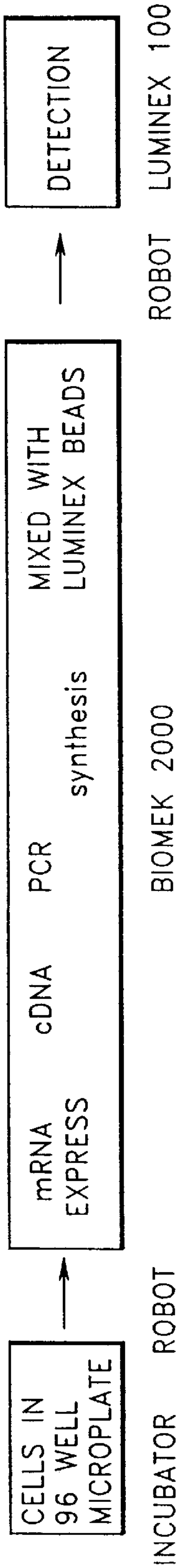
FIG. 7 shows a system for processing multiple samples using PCR and the liquid metal baths of the present disclosure.

A plurality of containers containing liquid metal will be employed in an automated system using a robotic liquid handler and dispenser such as the Biomek 2000 from Beckman Coulter (FIG. 7). In a preferred embodiment, three containers may be used at temperatures of 30–65° C., 65–85° C. and 85–100° C., respectively. The system will be enclosed in a plastic box-like container with purified air supplied through a HEPA filter. The system will also include a vacuum manifold for filtration, a temperature control unit and a temperature monitoring system for use during thermocycling. Using a kit such as the mRNA Express Kit, the workstation may be used for collection of cells from multi-well plates, cell lysis, mRNA purification, cDNA synthesis, and amplification by PCR without human intervention. After PCR, the GenePlate from the mRNA Express Kit is automatically heated at 94° C. and the solutions from each well are transferred to fresh microplates where capture oligonucleotide-immobilized Luminex beads and streptavidin-PE (dye) were aliquoted previously. The GenePlate is then transferred to the Luminex X-Y station for detection. Although sample preparation and Luminex detection each have ample and satisfactory throughput, the time limiting factor is PCR which can take 1–3 hours depending on individual applications. In one embodiment, the combined throughput of this system is 96 samples every 1–3 hours. Because 6–10 genes can be analyzed simultaneously in each well of the GenePlate, a total of 576–960 genes can be analyzed every 1–3 hours.

Ultra-high Throughput Gene Amplification Platform

In the high throughput model, a MegaCycler (Hudson Control) is placed next to the Biomek 2000. In a preferred embodiment, the MegaCycler can accommodate up to six GenePlates simultaneously and the Beckman Coulter ORCA robotic arm (or equivalent) transfers the GenePlates between the Biomek 2000, the MegaCycler, and the Luminex instruments.

Figure 8:
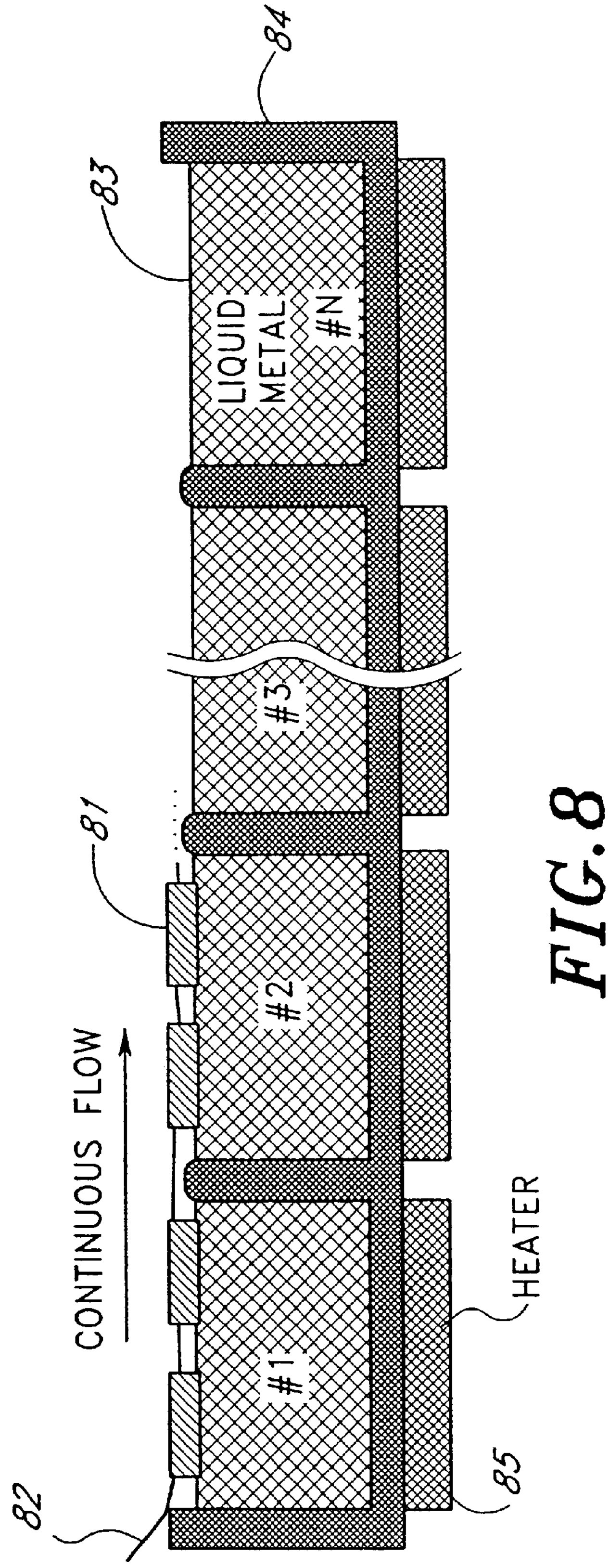
FIG. 8 is a schematic view showing an embodiment of a PCR continuous flow system using a liquid metal.

In the above, the time limiting factor is PCR which takes 1–3 hours for sufficient amplification. In one embodiment, a PCR factory includes, for example, 90 liquid metal baths for 30 cycles arranged in a linear assembly-line fashion. Each bath may have a length sufficient to accommodate one or two PCR plates. The number of liquid metal baths can freely be selected depending on the intended number of cycles. Because a liquid metal has excellent heat conductivity and heat transfer and allows PCR plates to flow thereon, it is possible to conduct a continuous flow system. This system allows analyzing 96 samples (576–960 genes) every 2 minutes. Surprisingly, this means that the human genome can be fully sequenced in less than one day. As shown in FIG. 8, PCR plates 81 are coupled in line with a string 82 which continuously moves the PCR plates in one direction. The PCR plates flows on top of a liquid metal 83 filling each bath 84 (#1 to #n). The baths 84 are arranged in line and are heated by a heater 85 provided at the bottom of the bath. Any heating method can be employed. Each bath 84 may hold 200cc to 1,000cc of the liquid metal 83.

Figure 9:
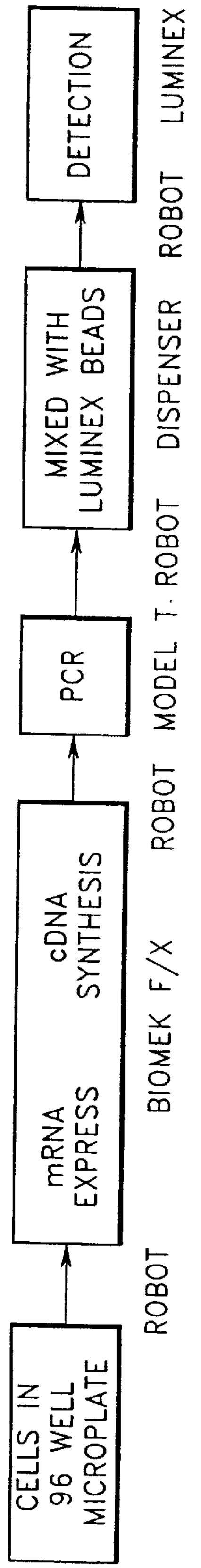
FIG. 9 shows a system for continuously processing multiple samples using PCR and the liquid metal baths of the present disclosure.

In an embodiment, by using the above continuous flow system, polynucleotide analyses can be conducted by arranging other systems upstream and downstream of the continuous flow system. FIG. 9 shows an example. From one end, a GenePlate, which already has cDNA synthesized from captured mRNA, is placed in the first bath, remains for 30–90 seconds and is then robotically transferred to the next bath. This protocol continues with each successive liquid metal bath. At the other end, PCR-completed GenePlates are removed every 30–90 seconds in a similar assembly line fashion. With this arrangement, the time limiting factors are the Biomek 2000 and the Luminex instrument. By switching to the superior Biomek F/X, a GenePlate can now be treated every two minutes. The current Luminex 100 instrument has only one nozzle, and requires approximately 10–20 minutes of processing time for each GenePlate. Additional Luminex 100 instruments could be incorporated into the system. In the above, each device can be of any type or model. One of ordinary skill in the art can readily obtain devices as necessary.

Uniformity of Temperature

The following Table 1 demonstrates the uniformity of temperature for the liquid metal bath compared to a commercially available thermocycler and a water bottle. It can be seen from the data that both variation at a given location in the heating apparatus and variation between locations within the heating apparatus are much less for the liquid metal bath than for a conventional thermocycler. For the liquid metal bath, variation in temperatures measured at 5 different locations is 74.5° C. to 73.1° C. or a range of 1.4° C. In contrast, the temperature variation for a conventional thermocycler measured at 5 locations is 71.3° C. to 68.9° C. or a range of 2.4° C. Likewise, the variability of temperature at any given point in the heating apparatus is greater for the conventional thermocycler than for the liquid metal bath. Variabilities as high as +/–3.3° C. are observed with the conventional thermocycler while the greatest variability with the liquid metal bath is +/–0.09° C. Clearly, the liquid metal bath of the presently claimed invention provides more precise temperature control compared to temperature regulators currently available.

Uniformity of temperature of a liquid metal bath can be improved by circulating the liquid metal in the bath. Circulation of the liquid metal can be created by natural convection, forced convection using a pump or megnetohydrodynamic power, vibration by physical force or megnetohydrodynamic power with DC current, etc. When using a PCR plate such as a microtiter plate, even if circulation becomes steady flow in the bath, the steady flow can easily be unsteady or turbulent when placing or submerging the plate in the liquid metal, resulting in a uniform temperature distribution.

TABLE 1

| | | Temperature uniformity | | |
|---|---|---|---|---|
| | Location of sensor | Control* (n = 7) | Liquid metal** (n = 7) | Thermocycler*** (n = 6) |
| Sensor 1 | upper left corner | 21.8 ± 0.05° C. | 73.1 ± 0.09° C. | 70.8 ± 0.97° C. |
| Sensor 2 | lower left corner | 21.7 ± 0.09° C. | 73.8 ± 0.08° C. | 71.0 ± 1.02° C. |
| Sensor 3 | upper right corner | 21.8 ± 0.09° C. | 74.0 ± 0.08° C. | 71.3 ± 1.11° C. |
| Sensor 4 | lower right corner | 21.6 ± 0.05° C. | 74.5 ± 0.00° C. | 71.2 ± 0.83° C. |
| Sensor 5 | middle | 21.7 ± 0.00° C. | 74.2 ± 0.05° C. | 68.9 ± 3.33° C. |

*5 sensors are placed in the same water bottle.
**5 sensors are placed in the different locations within the same liquid metal bath
***5 sensors are placed in the different wells of heat block of commercially available model 480 thermocycler (PR Bio).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An apparatus for temperature control of samples, comprising:

at least one container containing liquid metal, said container having an upper open area where the liquid metal thermally contacts one or more of the samples for temperature control thereof; and a temperature control device for heating the liquid metal at least over a temperature range from about 65° C. to about 85° C., whereby said liquid metal remains in a liquid state and does not significantly vaporize at a temperature within said range, wherein said metal is in a liquid state throughout said temperature range.

2. The apparatus of claim 1 wherein the container containing liquid metal is placed in contact with the heat block of a thermal cycler.

3. The apparatus of claim 1 wherein the container containing liquid metal is a metal container.

4. The apparatus of claim 1 wherein the container containing liquid metal is a plastic container.

5. The apparatus of claim 1 wherein the liquid metal is a gallium-indium alloy.

6. The apparatus of claim 5 wherein the gallium-indium alloy comprises 75.5% gallium and 24.5% indium.

7. The apparatus of claim 1 which comprises a plurality of containers containing liquid metal and one sample container.

8. The apparatus of claim 7 further comprising a robotic arm for moving the sample containers between the plurality of containers containing liquid metal.

9. The apparatus of claim 1 wherein the liquid metal is moved throughout the container by magnetohydrodynamics.

10. The apparatus of claim 1 wherein the liquid metal is moved throughout the container by a pump.

11. The apparatus of claim 1 wherein gravity is used to move the liquid metal.

12. The apparatus of claim 1 wherein a plurality of containers containing liquid metal are operably linked to a robotic liquid handler and dispenser.

13. The apparatus of claim 12 wherein three containers containing liquid metal are maintained at 30–65° C., 65–85° C. and 85–100° C., respectively.

14. A method of incubating one or more biological/chemical samples in one or more containers at a predetermined temperature, comprising contacting the one or more containers with liquid metal at the pre-determined temperature for a given time period, wherein said metal is in a liquid state at least over a temperature range from about 65° C. to about 85° C., and wherein said liquid metal remains in a liquid state and does not significantly vaporize at a temperature within said range.

15. The method of claim 14, wherein the biological/chemical samples in one or more containers are moved manually to contact the liquid metal.

16. The method of claim 14, wherein a robotic arm moves the biological/samples in one or more containers to contact the liquid metal.

17. The method of claim 14, wherein the predetermined temperatures for said containers are 30–65° C., 65–85° C. and 85–100° C., respectively.

18. A method of varying the temperature of a biological/chemical sample, comprising:

(a) incubating a container containing the biological/chemical sample in liquid metal at a first pre-determined temperature for a given time period; and (b) incubating the container containing the biological/chemical sample in liquid metal at a second pre-determined temperature which is different from the first pre-determined temperature.

19. The method of claim 18, wherein the temperature change is affected by replacing liquid metal at the first predetermined temperature with liquid metal at the second predetermined temperature.

20. The method of claim 19, wherein the liquid metal is replaced by moving using magnetohydrodynamics.

21. The method of claim 20, wherein the magnetohydrodynamics is in AC mode.

22. The method of claim 20, wherein the magnetohydrodynamics is in DC mode.

23. The method of claim 19, wherein the liquid metal is moved by a pump.

24. The method of claim 19 wherein gravity is used to move the liquid metal.

25. The method of claim 18 wherein the liquid metal is a gallium-indium alloy.

26. The method of claim 25 wherein the gallium-indium alloy comprises 75.5% gallium and 24.5% indium.

27. A method of carrying out polymerase chain reaction (PCR), wherein one PCR cycle comprises:

denaturing a polynucleotide sample in thermal contact with liquid metal at a temperature of about 90–98° C. for about 10–90 seconds;

hybridizing oligonucleotide primers to the denatured polynucleotide sample in thermal contact with liquid metal at a temperature of about 30–65° C. for about 1–2 minutes; and synthesizing a new polynucleotide strand incorporating the oligonucleotide primer and using the denatured polynucleotide sample as a template for a polymerase in thermal contact with liquid metal at a temperature of about 70–75° C. for about 30 seconds to 5 minutes.

28. An apparatus for temperature control of samples, comprising:

at least one container containing liquid metal, said container having an upper open area where the liquid metal thermally contacts one or more of the samples for temperature control thereof; and a temperature control device for heating the liquid metal, whereby said liquid metal remains in a liquid state and does not significantly evaporate during heating, and wherein said container containing liquid metal is a plastic container.

29. An apparatus for temperature control of samples, comprising:

at least one container containing liquid metal, said container having an upper open area where the liquid metal thermally contacts one or more of the samples for temperature control thereof; and a temperature control device for heating the liquid metal whereby said liquid metal remains in a liquid state and does not significantly evaporate during heating, wherein said liquid metal is a gallium-indium alloy.

30. The apparatus of claim 29, wherein the gallium-indium alloy comprises 75.5% gallium and 24.5% indium.

31. An apparatus for temperature control of samples, comprising a plurality of containers containing liquid metal and at least one sample container, wherein at least one container containing liquid metal having an upper open area where the liquid metal thermally contacts one or more of the sample containers for temperature control thereof;

a temperature control device for heating the liquid metal, whereby said liquid metal remains in a liquid state and does not significantly evaporate during heating, and a robotic arm for moving the sample containers between the plurality of containers containing liquid metal.

32. The apparatus for temperature control of samples, comprising:

at least one container containing liquid metal, said container having an upper open area where the liquid metal thermally contacts one or more of the samples for temperature control thereof; and a temperature control device for heating the liquid metal, whereby said liquid metal remains in a liquid state and does not significantly evaporate during heating, wherein the liquid metal is moved throughout the container by magnetohydrodynamics.

33. An apparatus for temperature control of samples, comprising:

at least one container containing liquid metal, said container having an upper open area where the liquid metal thermally contacts one or more of the samples for temperature control thereof; and a temperature control device for heating the liquid metal, whereby said liquid metal remains in a liquid state and does not significantly evaporate during heating, and wherein a plurality of containers containing liquid metal are operably linked to a robotic liquid handler and dispenser.

34. The apparatus of claim 33, wherein three containers containing liquid metal are maintained at 30–65° C., 65–85° C. and 85–100° C., respectively.

35. A method of incubating one or more biological/chemical samples at a predetermined temperature comprising contacting the one or more biological/chemical samples with a container containing liquid metal at the predetermined temperature for a given time period, wherein a robotic arm moves the biological/chemical samples between a plurality of containers containing liquid metal.

36. The method of claim 35, wherein the predetermined temperatures for said plurality of containers are 30–65° C., 65–85° C. and 85–100° C., respectively.

37. A method of varying the temperature of a sample in a single container, comprising:

(a) incubating a biological/chemical sample in contact with a container containing liquid metal at a first predetermined temperature for a given time period;

(b) changing the temperature of the liquid metal to a second predetermined temperature which is different from the predetermined temperature of step (a);

(c) repeating steps (a) and (b) until all desired incubations have occurred; and wherein the temperature change is affected by replacing liquid metal at the first predetermined temperature with liquid metal at the second predetermined temperature, and wherein the liquid metal is moved throughout the container containing liquid metal by magnetohydrodynamics.

38. The method of claim 37, wherein the magnetohydrodynamics is in AC mode.

39. The method of claim 37, wherein the magnetohydrodynamics is in DC mode.

40. A method of varying the temperature of a sample in a single container, comprising:

(a) incubating a biological/chemical sample in contact with a container containing liquid metal at a first predetermined temperature for a given time period;

(b) changing the temperature of the liquid metal to a second predetermined temperature which is different from the predetermined temperature of step (a);

(c) repeating steps (a) and (b) until all desired incubations have occurred; and wherein the liquid metal is a gallium-indium alloy.

41. The method of claim 40, wherein the gallium-indium alloy comprises 75.5% gallium and 24.5% indium.

42. The method of claim 18, wherein the incubating at the first pre-determined temperature and the incubating at the second pre-determined temperature are performed in a single liquid metal bath, said method additionally comprising changing the temperature of the liquid metal in said container from the first pre-determined temperature to the second pre-determined temperature between the incubating at the first temperature and the incubating at the second temperature.

* * * * *